United States Patent
Funderburk

(10) Patent No.: US 10,413,739 B2
(45) Date of Patent: Sep. 17, 2019

(54) WRAP-AROUND CONTAINER FOR CONTROL MODULE OF ELECTRICAL STIMULATION SYSTEMS AND METHODS OF MAKING AND USING

(71) Applicant: Boston Scientific Neuromodulation Corporation, Valencia, CA (US)

(72) Inventor: Jeffery Van Funderburk, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 749 days.

(21) Appl. No.: 15/006,988

(22) Filed: Jan. 26, 2016

(65) Prior Publication Data

US 2016/0220826 A1    Aug. 4, 2016

Related U.S. Application Data

(60) Provisional application No. 62/110,101, filed on Jan. 30, 2015.

(51) Int. Cl.
*A61N 1/37* (2006.01)
*A61N 1/375* (2006.01)
(Continued)

(52) U.S. Cl.
CPC ......... *A61N 1/3754* (2013.01); *A61N 1/3758* (2013.01); *H05K 5/0086* (2013.01);
(Continued)

(58) Field of Classification Search
CPC .. A61N 1/0551; A61N 1/3754; A61N 1/3758; H05K 13/00; H05K 5/0086; H05K 5/0247; H05K 5/04; H05K 5/06
See application file for complete search history.

(56) References Cited

U.S. PATENT DOCUMENTS 6,181,969 B1    1/2001  Gord
6,516,227 B1    2/2003  Meadows et al.
(Continued)

OTHER PUBLICATIONS

U.S. Appl. No. 62/077,784, filed Nov. 10, 2014.
(Continued)

*Primary Examiner* — Amanda K Hulbert
(74) *Attorney, Agent, or Firm* — Lowe Graham Jones PLLC; Bruce E. Black

(57) ABSTRACT

An implantable control module for an electrical stimulation system includes a connector housing including a connector having one or more ports and connector contacts disposed within the connector; a metal electronics housing coupled to the connector housing; an electronic subassembly disposed within the metal electronics housing; and a feedthrough assembly disposed between the connector housing and the metal electronics housing and including at least one non-conductive block and conductive feedthroughs extending through the at least one non-conductive block and electrically coupling the electronic subassembly to the connector contacts. The metal electronics housing includes a metal sheet bent to form at least a portion of the first major surface and at least a portion of the second major surface. The first major surface has a length and includes a first sealed seam extending along an entirety of the length of the first major surface.

20 Claims, 7 Drawing Sheets

(51) Int. Cl.
- *H05K 13/00* (2006.01)
- *H05K 5/00* (2006.01)
- *H05K 5/02* (2006.01)
- *H05K 5/04* (2006.01)
- *H05K 5/06* (2006.01)
- *A61N 1/05* (2006.01)

(52) U.S. Cl.
CPC ............ *H05K 5/0247* (2013.01); *H05K 5/04* (2013.01); *H05K 5/06* (2013.01); *H05K 13/00* (2013.01); *A61N 1/0551* (2013.01)

(56) References Cited

U.S. PATENT DOCUMENTS

| | | |
|---|---|---|
| 6,609,029 B1 | 8/2003 | Mann et al. |
| 6,609,032 B1 | 8/2003 | Woods et al. |
| 6,741,892 B1 | 8/2004 | Meadows et al. |
| 7,244,150 B1 | 7/2007 | Brase et al. |
| 7,437,193 B2 | 10/2008 | Parramon et al. |
| 7,489,516 B2 | 2/2009 | Lacey |
| 7,672,734 B2 | 3/2010 | Anderson et al. |
| 7,761,165 B1 | 7/2010 | He et al. |
| 7,803,021 B1 | 9/2010 | Brase |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 8,682,439 B2 | 3/2014 | DeRohan et al. |
| 2003/0199942 A1 | 10/2003 | Nielsen et al. |
| 2007/0150036 A1 | 6/2007 | Anderson |
| 2008/0071320 A1 | 3/2008 | Brase |
| 2008/0294207 A1* | 11/2008 | Kast ............ A61L 31/022 607/2 |
| 2010/0274309 A1 | 10/2010 | Knipfer et al. |
| 2011/0022100 A1 | 1/2011 | Brase et al. |
| 2012/0053646 A1 | 3/2012 | Brase et al. |
| 2012/0071937 A1 | 3/2012 | Sundaramurthy et al. |
| 2012/0259386 A1 | 10/2012 | DeRohan et al. |
| 2013/0206472 A1 | 8/2013 | Stevenson et al. |
| 2014/0214130 A1* | 7/2014 | Lopez ............ A61N 1/3754 607/59 |
| 2015/0051676 A1 | 2/2015 | Funderburk |
| 2015/0051677 A1 | 2/2015 | Marnfeldt |
| 2015/0209575 A1 | 7/2015 | Black |
| 2016/0059019 A1 | 3/2016 | Malinowski et al. |

OTHER PUBLICATIONS

U.S. Appl. No. 62/077,762, filed Nov. 10, 2014.
International Search Report and Written Opinion for PCT/US2016/014962 dated Apr. 14, 2016.

\* cited by examiner

WRAP-AROUND CONTAINER FOR CONTROL MODULE OF ELECTRICAL STIMULATION SYSTEMS AND METHODS OF MAKING AND USING

CROSS-REFERENCE TO RELATED APPLICATIONS

This application claims the benefit under 35 § 119(e) of U.S. Provisional Patent Application Ser. No. 62/110,101, filed Jan. 30, 2015, which is incorporated herein by reference.

FIELD

The present invention is directed to the area of implantable electrical stimulation systems and methods of making and using the systems. The present invention is also directed to implantable electrical stimulation leads having a control module with a container made from a planar plate of metal, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an implantable control module for an electrical stimulation system. The control module includes a connector housing including a connector having one or more ports each configured and arranged to receive a proximal end of a lead or lead extension and connector contacts disposed within the connector and configured and arranged for making contact with terminals disposed on the proximal end portion of the lead or lead extension; a metal electronics housing coupled to the connector housing and having a first major surface and a second major surface opposite the first major surface; an electronic subassembly disposed within the metal electronics housing; and a feedthrough assembly disposed between the connector housing and the metal electronics housing and including at least one non-conductive block and a plurality of conductive feedthroughs extending through the at least one non-conductive block and electrically coupling the electronic subassembly to the connector contacts. The metal electronics housing includes a metal sheet bent to form at least a portion of the first major surface and at least a portion of the second major surface. The first major surface has a length and includes a first sealed seam extending along an entirety of the length of the first major surface.

In at least some embodiments, the metal electronic housing further includes a second metal sheet bent to form at least a portion of the first major surface and at least a portion of the second major surface, the metal electronic housing further includes a second sealed seam extending along an entirety of the length of the second major surface. In at least some embodiments, the first sealed seam and the second sealed seam both join the first bent metal sheet to the second bent metal sheet.

In at least some embodiments, the first bent metal sheet includes a first edge and a second edge, where the first sealed seam joins the first edge to the second edge. In at least some embodiments, the metal electronics housing further includes a bottom plate attached to the first bent metal sheet. In at least some embodiments, the feedthrough assembly includes a metal flange disposed around the at least one non-conductive block and attached to the metal electronics housing. In at least some embodiments, the first bent metal sheet consists of grade 23 titanium alloy. In at least some embodiments, the first bent metal sheet includes at least one interlocking feature along the first sealed seam. In at least some embodiments, the at least one interlocking feature is a dovetailed feature.

Another embodiment is an implantable control module for an electrical stimulation system that includes a connector housing including a connector having one or more ports each configured and arranged to receive a proximal end of a lead or lead extension and connector contacts disposed within the connector and configured and arranged for making contact with terminals disposed on the proximal end of the lead or lead extension; a metal electronics housing coupled to the connector housing and consisting essentially of a single metal sheet bent to produce at least a first major surface, where the first major surface has a length and includes a sealed seam extending along an entirety of the length of the first major surface; an electronic subassembly disposed within the metal electronics housing; and a feedthrough assembly disposed between the connector housing and the metal electronics housing and including at least one non-conductive block and a plurality of conductive feedthroughs extending through the at least one non-conductive block and electrically coupling the electronic subassembly to the connector contacts.

In at least some embodiments, the single metal sheet includes a first edge and a second edge, where the first sealed seam joins the first edge to the second edge. In at least some embodiments, the metal sheet forms a second major surface opposite the first major surface, at least two side surfaces coupling the first and second major surfaces, and a bottom piece coupling the first major surface to the second major surface and coupling two of the at least two side surfaces. In at least some embodiments, the feedthrough assembly includes a metal flange disposed around the at least one non-conductive block and attached to the metal electronics housing. In at least some embodiments, the single metal sheet consists of grade 23 titanium alloy. In at least some embodiments, the single metal sheet includes at least one interlocking feature formed along each of at least two edges of the single metal sheet. In at least some embodiments, the at least one interlocking feature is a dovetailed feature.

Yet another embodiment is an electrical stimulation system that includes any of the control modules described above; and a lead coupleable to the control module including a proximal end portion, a distal end portion, electrodes disposed along the distal end portion, and terminals disposed along the proximal end portion and electrically coupled to the plurality of electrodes.

A further embodiment is a method of making an implantable control module of an electrical stimulation system. The method includes providing a single flat metal sheet; bending the single flat metal sheet to form an electronics housing with a seam, along a length of the first major surface of the electronics housing; sealing the seam; disposing an electronics subassembly within the electronics housing; and coupling a feedthrough assembly and a connector housing to the electronics housing.

In at least some embodiments, the single flat metal sheet includes at least one interlocking feature formed along each of at least two edges of the single flat metal sheet, where bending the single flat metal sheet includes interlocking the at least one interlocking feature of the at least two edges.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having a control module with a container made from a planar plate of metal, as well as methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
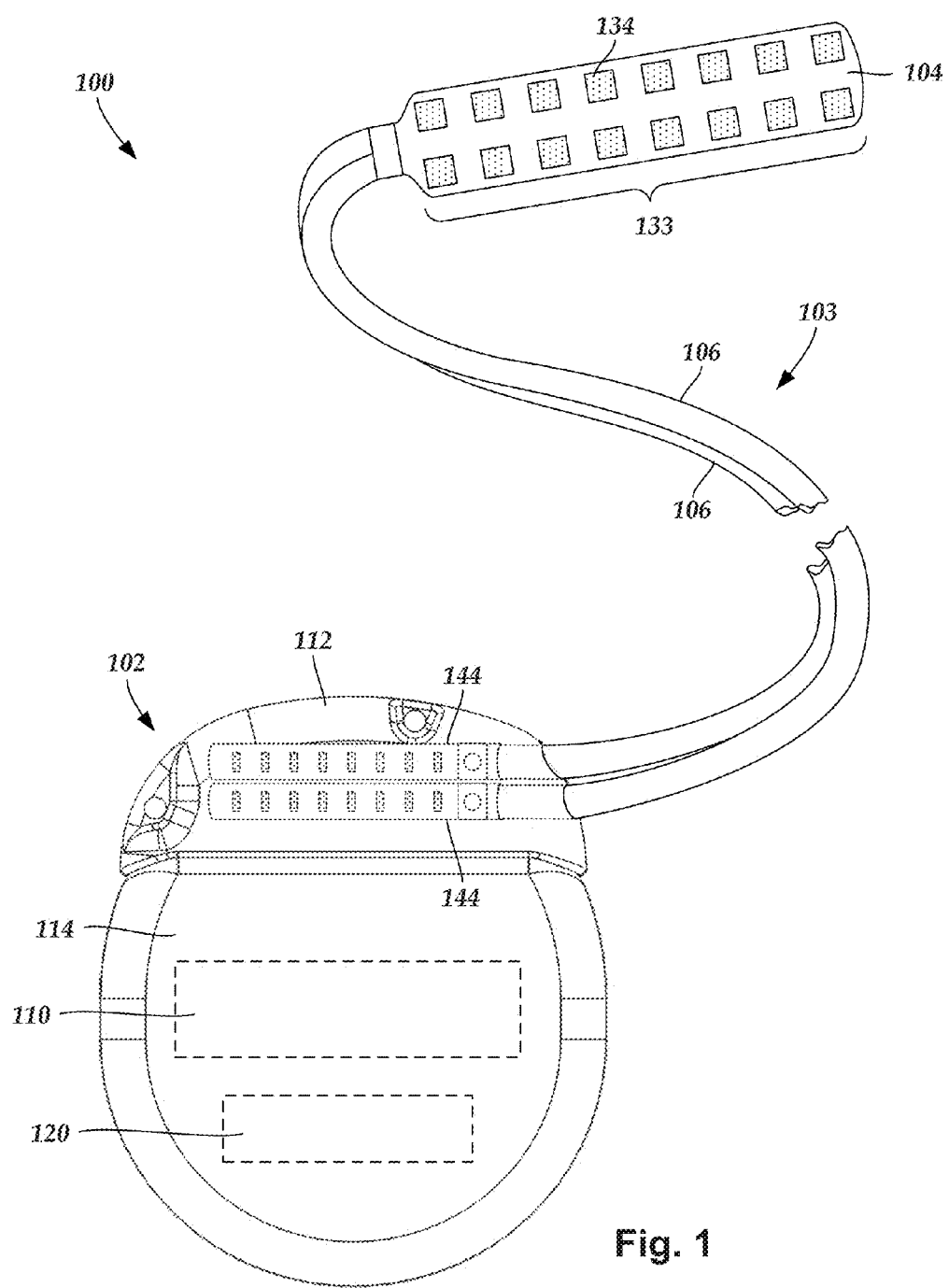
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIGS. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
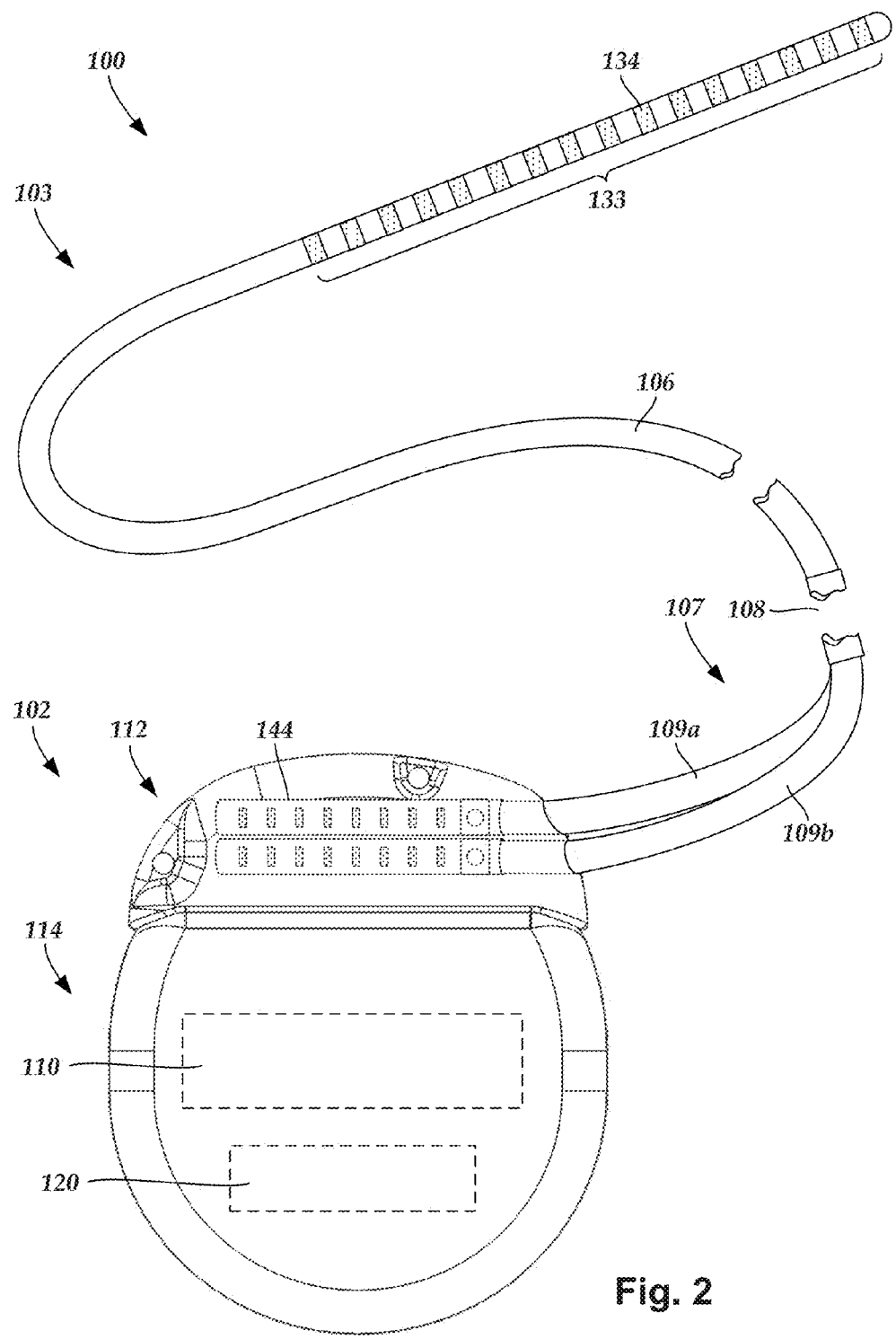
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a metal electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
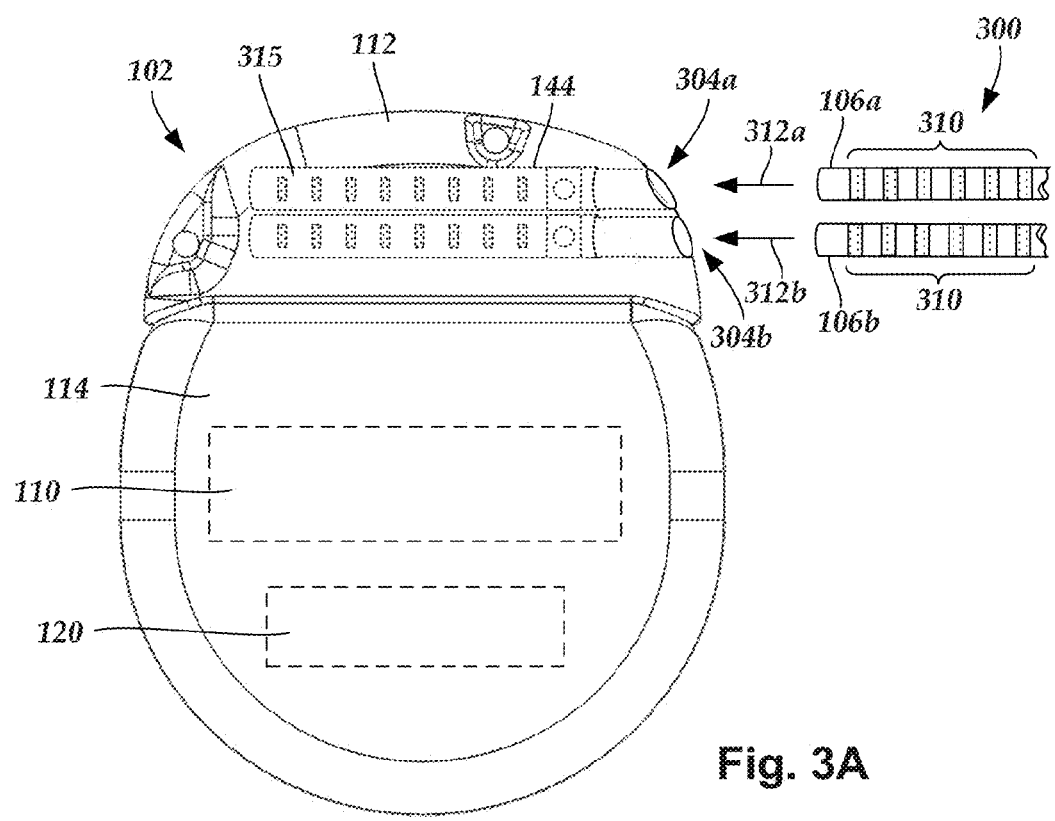
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 315 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead. bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, tor example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 315, disposed within each port 304a and 304b. When the elongated device 300 is inserted into the ports 304a and 304b, the connector contacts 315 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

In other embodiments, the lead may be permanently coupled to the control module. In at least some of these embodiments, the conductors of the lead may feed directly into the connector for attachment to conductive feedthroughs or even feed directly into the electronics housing.

Figure 3B:
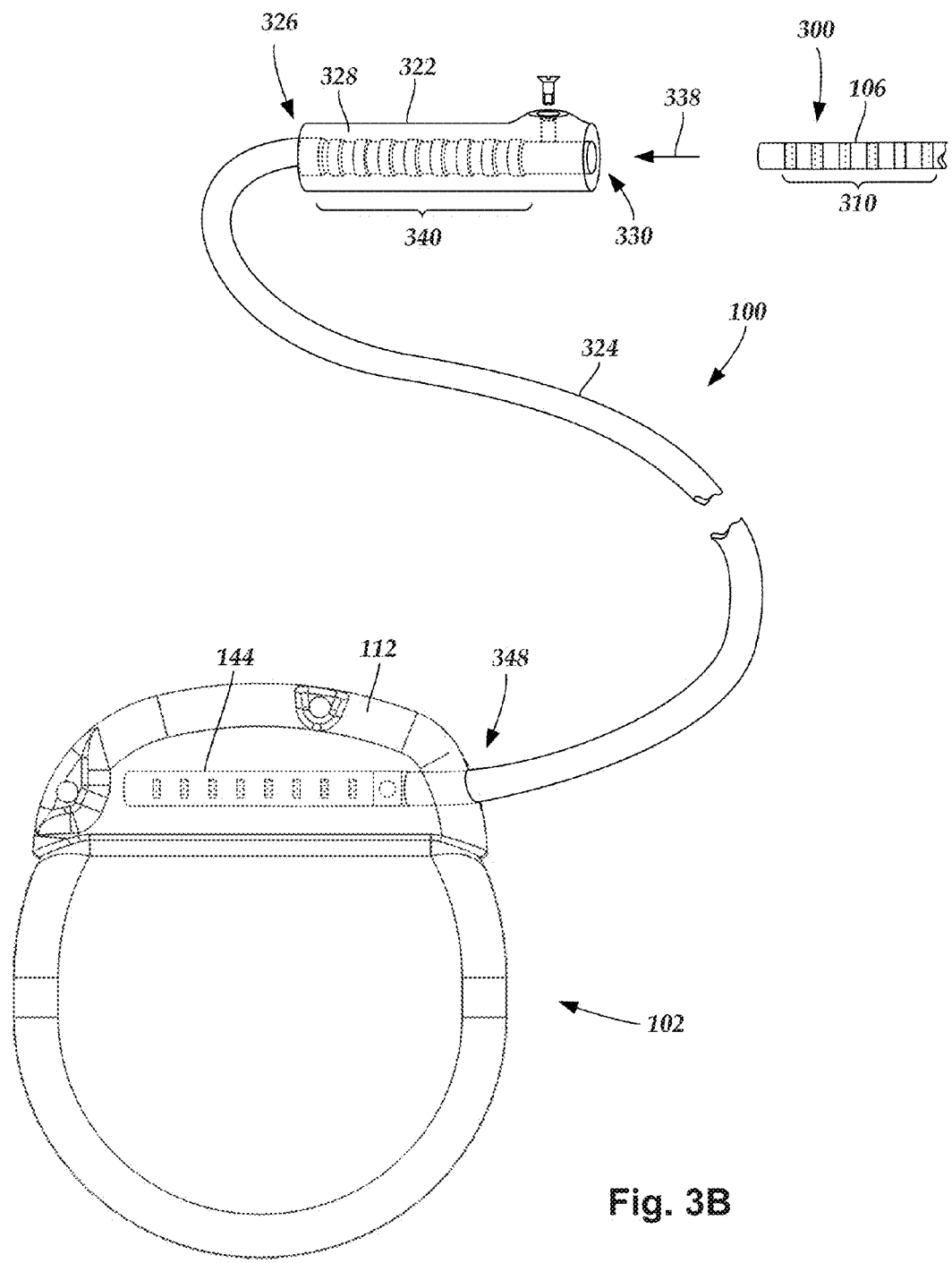
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

The electronics housing of the control module can be formed using metal (including alloys). Some metals can be readily drawn or molded into the desired shape for the electronics housing. Other metals, such as grade 23 titanium alloy (Which contains, for example, 6% aluminum, 4% vanadium, 0.13% (maximum) oxygen), however, are more difficult to draw or mold. For example, it may be difficult in such metals to form small radii features that are suitable for the control module. These metals may have desired mechanical or electrical properties. For example, grade 23 titanium alloy has desirable resistivity properties (e.g., higher resistance to reduce eddy currents in the housing). These properties can be particularly useful for control modules with a rechargeable battery or an antenna to receive programming instructions.

Figure 4:
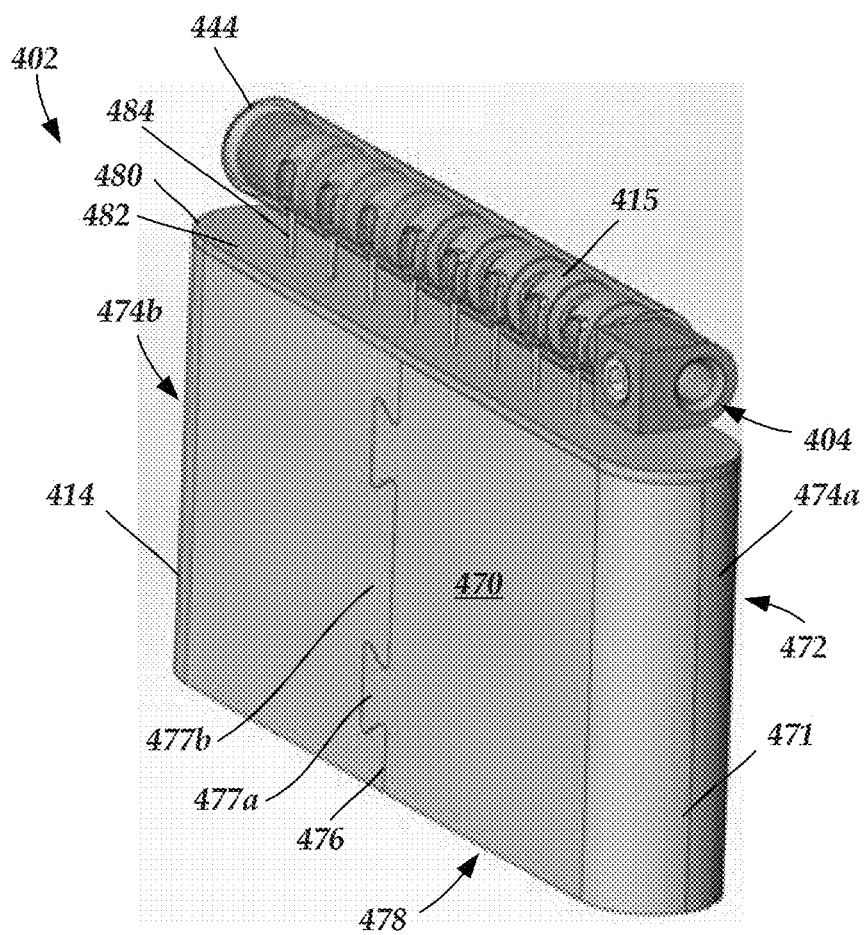
FIG. 4 is a schematic perspective view of one embodiment of a control module, with a portion of the connector housing removed for illustration purposes, according to the invention.

An electronics housing can be formed that is not drawn or molded, but is instead formed from one or more flat or bent sheets of metal that are joined at one or more seams along a length of the electronics housing. FIG. 4 illustrates one embodiment of a control module 402 (although the full connector housing is not illustrated in FIG. 4 for clarity) with a metal electronics housing 414 having a first major surface 470, a second major surface 472 opposite the first major surface, and at least two side surfaces 474a, 474b coupling the first and second major surfaces. The metal electronics housing is formed from one or more bent metal sheets 471 with each bent metal sheet forming at least a portion of the first major surface, at least a portion of the second major surface, and at least one of the side surfaces. Any of these surfaces 470, 472, 474a, 474b can be flat (for example, surface 470, 472) or curved (for example, surfaces 474a, 474b) In at least some embodiments, the metal electronics housing 414 can be made from one or more flat metal pieces that is/are bent to form bent metal sheet(s) 471.

Although electronics housing 414 is illustrated with two major surfaces and at least two side surfaces, other electronics housings can be formed using one or more bent metal sheets. For example, in some embodiments, an electronics housing may have only two major surfaces with no side surfaces or a single side surface. In other embodiments, an electronics housing may be a cylinder, sphere, ovoid, or other construct with only one major surface.

The metal electronics housing 414 has a sealed seam 476 extending along the entirety of the length of the First major surface. Optionally, the metal electronics housing can have a second sealed seam (not shown) that extends along the entirety of the length of the second major surface; for example, if the metal electronics housing is formed from at least two bent metal sheets. An electronic subassembly (see, FIGS. 1-3A, electronics subassembly 110) is disposed within the metal electronics housing 414. In at least some embodiments, a power source (see, FIGS. 1-3a, power source 120) is also disposed within the metal electronics housing 414. In at least some embodiments, the metal electronics housing 414 also includes a bottom plate 478 that is integrally formed with the one or more bent metal sheets 471 or is attached, for example, by welding to the one or more bent metal sheets.

The bent metal sheet 471 can be cut into the desired shape using any suitable methods including, but not limited to, stamping, die cutting, laser cutting, or the like. The metal sheet 471 can be bent prior to cutting or can be bent after cutting or between cuts. Moreover, the bent metal sheet can have one bend or multiple bends. In some embodiments, a laser or other device can be used to etch the bent metal sheet 471 at corners or other sections of the piece to provide relief, to promote a tighter radii, or to reduce bowing on straight sections. In some embodiments, a stiffener (not shown), such as metal or rigid plastic strips or bands, can be positioned on portions of the bent metal sheet 471 to reduce or prevent bowing of sections that are intended to be flat when the flat metal piece is formed into the electronic housing.

The bent metal sheet 471 can be made of any suitable metal material (including alloys). Examples of suitable materials include grade 23 titanium alloy, grade 1 titanium alloy (ASME SB-265, incorporated herein by reference, describes this material), grade 9 titanium alloy (includes, for example, 3% aluminum and 2.5% vanadium), grade 5 titanium alloy (or titanium 6/4 or 6-4—for example, 6% aluminum, 4% vanadium, 0.25% (maximum) iron, 0.2% (maximum) oxygen), titanium, other titanium alloys, and the like.

In other embodiments, the electronics housing can be made using one or more bent metal sheets that can also be stretched or otherwise worked in sections of the housing. For example, such a housing may have a stretched portion that to accommodate large or tall components within the housing.

In at least some embodiments, the sealed seam 476 can include interlocking features 477a, 477b that fit together and can be welded (for example, laser welded) together or otherwise coupled, as illustrated in FIG. 4. The illustrated interlocking features 477a, 477b have a dovetail shape, but it will be understood that the interlocking features can have other suitable shapes. In some embodiments, the seam 476 includes one, two, three, or more interlocking features. Prior to forming the seam, the interlocking features 477a, 477b can take the form of projections and corresponding cutouts.

In some embodiments, the metal sheet on one side of the seam can include one or more projections and the metal sheet on the other side of the seam can include one or more cutouts. In other embodiments, the metal sheet on one side of the seam can include both one or more projections and one or more cutouts and the metal sheet on the other side of the seam includes corresponding cutout(s) and projection(s), as illustrated in FIG. 4.

The control module also includes a connector housing (see, FIGS. 1-3A for connector housing 112) coupled to the metal electronics housing 414. The connector housing includes a connector 444 having one or more ports 404 which can each receive a proximal end of a lead or lead extension and connector contacts 415 disposed within the connector for making contact with terminals disposed on the proximal end of the lead or lead extension. Examples of connectors and connector housing can be found at, for example, U.S. Pat. Nos. 7,244,150; 7,489,516; 7,803,021; and 8,682,439; U.S. Patent Application Publications Nos. 2008/0071320; 2011/0022100; 2012/0053646; and 2012/0071937; U.S. patent application Ser. No. 14/457,703; and U.S. Provisional Patent Applications Ser. Nos. 61/932,074; 62/044,050; 62/077,762; and 62/077,784, all of which are incorporated herein by reference.

The control module 402 further includes a feedthrough assembly 480 disposed between the connector housing and the metal electronics housing 414. The feedthrough assembly 480 includes a feedthrough block 482 and conductive feedthroughs 484 extending through the feedthrough block and electrically coupling the electronic subassembly (see, FIGS. 1-3A, electronics subassembly 110) to the connector contacts 444. The feedthrough block 482 includes at least one non-conductive block through which the conductive feedthroughs 484 pass. This non-conductive block can be attached (for example, by brazing) to the connector housing or electronics housing (or both) or the non-conductive block can be attached to a metal flange (for example, by brazing) which is attached (for example, by laser welding) to the connector housing or electronics housing (or both). Examples of feedthrough assemblies can be found at, for example, U.S. Pat. Nos. 7,244,150 and 7,803,021; U.S. Patent Application Publication No. 2014/0214130; and U.S. patent application Ser. No. 14/457,674, all of which are incorporated herein by reference. In some embodiments, the feedthrough assembly can utilize multiple non-conductive blocks. For example, each conductive feedthrough may be associated with its own non-conductive block or sets of conductive feedthroughs may be associated with different non-conductive blocks. In at least some embodiments, the non-conductive block may be circuit board, flex circuit, or other non-conductive substrate or may be a block of ceramic or other non-conductive material.

In other embodiments, the feedthrough assembly may be located along the seam 476. The feedthrough assembly will then also be part of the seal of the seam. In yet other embodiments, the feedthrough assembly may be located at an opening in the bent metal sheet 471.

Figure 5:
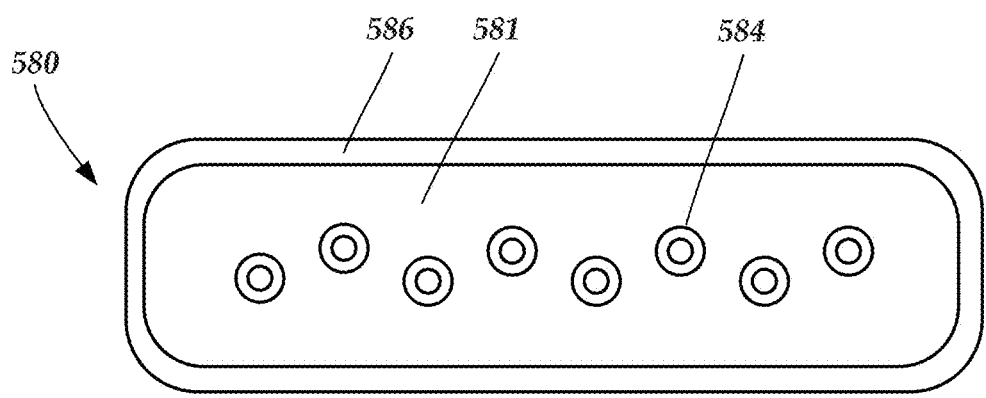
FIG. 5 is a schematic top view of one embodiment of a feedthrough assembly, according to the invention.

FIG. 5 illustrates one embodiment of a feedthrough assembly 580 that includes at least one ceramic block 581 with a number of feedthrough pins 584 passing through the at least one ceramic block 581 to electrically couple to the electronic subassembly and the connector contacts. A metal flange 586 is disposed around the periphery of the ceramic block 581. The metal flange 586 is connected to the ceramic block 581 using a braze joint or any other suitable arrangement.

Figure 6A:
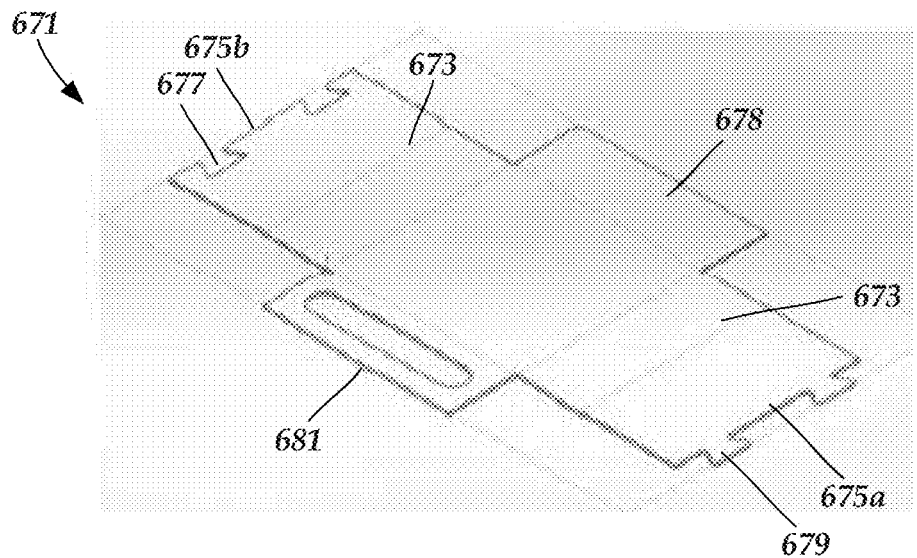
FIG. 6A is a schematic perspective view of one embodiment of a single flat metal piece that can be made into an electronics housing of a control module, according to the invention.

In at least some embodiments, an electronics housing can be formed by bending at least a portion of a flat piece of metal into the desired shape. FIG. 6A illustrates a single flat metal piece 671 that can be formed by bending into a portion of the electronics housing 614, as illustrated FIG. 6B. The flat metal piece 671 can be cut into the desired shape using any suitable methods including, but not limited to, stamping, die cutting, laser cutting, or the like. In some embodiments, a laser or other device can be used to etch the flat metal piece 671 at corners or other sections of the piece to provide relief, to promote a tighter radii, or to reduce bowing on straight sections.

In other embodiments, the electronics housing can be made using a flat piece of metal that can also be stretched or otherwise worked in sections of the housing. For example, such a housing may have a stretched portion that to accommodate large or tall components within the housing.

The flat metal piece 671 can be made of any suitable metal material (including alloys). Examples of suitable materials include grade 23 titanium alloy, grade 1 titanium alloy (ASME SB-265, incorporated herein by reference, describes this material), grade 9 titanium alloy (includes, for example, 3% aluminum and 2.5% vanadium), grade 5 titanium alloy (or titanium 6/4 or 6-4—for example, 6% aluminum, 4% vanadium, 0.25% (maximum) iron, 0.2% (maximum) oxygen), titanium, other titanium alloys, and the like.

Figure 6B:
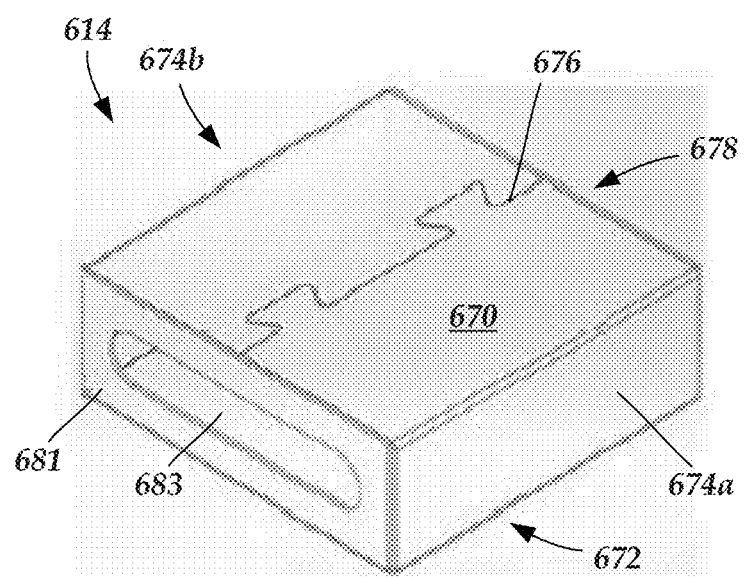
FIG. 6B is a schematic perspective view of an electronics housing of a control module made from the single flat metal piece of FIG. 6A, according to the invention.

In at least some embodiments, the flat metal piece 671 can include one or more pairs of interlocking edges 675a, 675b Which include interlocking features such as projections 679 and corresponding cutouts 677 that fit together and can be welded (for example, laser welded) together or otherwise coupled, as illustrated in FIG. 6B, to form a seam 676 that extends along a length of a first major surface 670. The electronics housing 644 also has a second major surface 672 and at least two side surfaces 674a, 674b between the first and second major surfaces. The projections 679 and cutouts 677 have a dovetail shape, but it will be understood that the projections and cutouts can have other suitable shapes. In some embodiments, one edge 675a includes one, two, three, or more projections 679 and the other edge 675b includes corresponding one, two, three, or more cutouts 677, as illustrated in FIG. 6A. In other embodiments, a seam can include both one or more projections and one or more cutouts and the other seam include corresponding cutout(s) and projection(s).

Although electronics housing 614 is illustrated with two major surfaces and at least two side surfaces, other electronics housings can be formed using a flat metal piece. For example, in some embodiments, an electronics housing may have only two major surfaces with no side surfaces or a single side surface. In other embodiments, an electronics housing may be a cylinder, sphere, ovoid, or other construct with only one major surface.

The shape of the flat metal piece 671 is designed around multiple bend lines 673 where the flat metal piece 671 is to be bent to form the electronics housing 614 of the control module. In some embodiments, a stiffener (not shown) can be positioned on portions of the flat metal piece 671 to reduce or prevent bowing of sections that are intended to be flat when the flat metal piece is formed into the electronic housing.

The flat metal piece 671 optionally has a portion that forms a bottom piece 678 for the control electronics housing 614. The flat metal piece 671 optionally has a portion that forms a top piece 681 for the control electronics housing 614. The top piece 681 should include at least one opening 683 through which feedthrough contacts can pass. In at least some embodiments, a feedthrough assembly (such as feedthrough assembly 480 in FIG. 4) can be positioned on, and coupled to, the top piece 681. The electronics housing 614 can be utilized with the connector 444 of FIG. 4 or another other suitable connector or connector housing.

In other embodiments, the feedthrough assembly may be located along the seam 676. The feedthrough assembly will then also be part of the seal of the seam. In yet other embodiments, the feedthrough assembly may be located at an opening in the metal piece 671.

Figure 7:
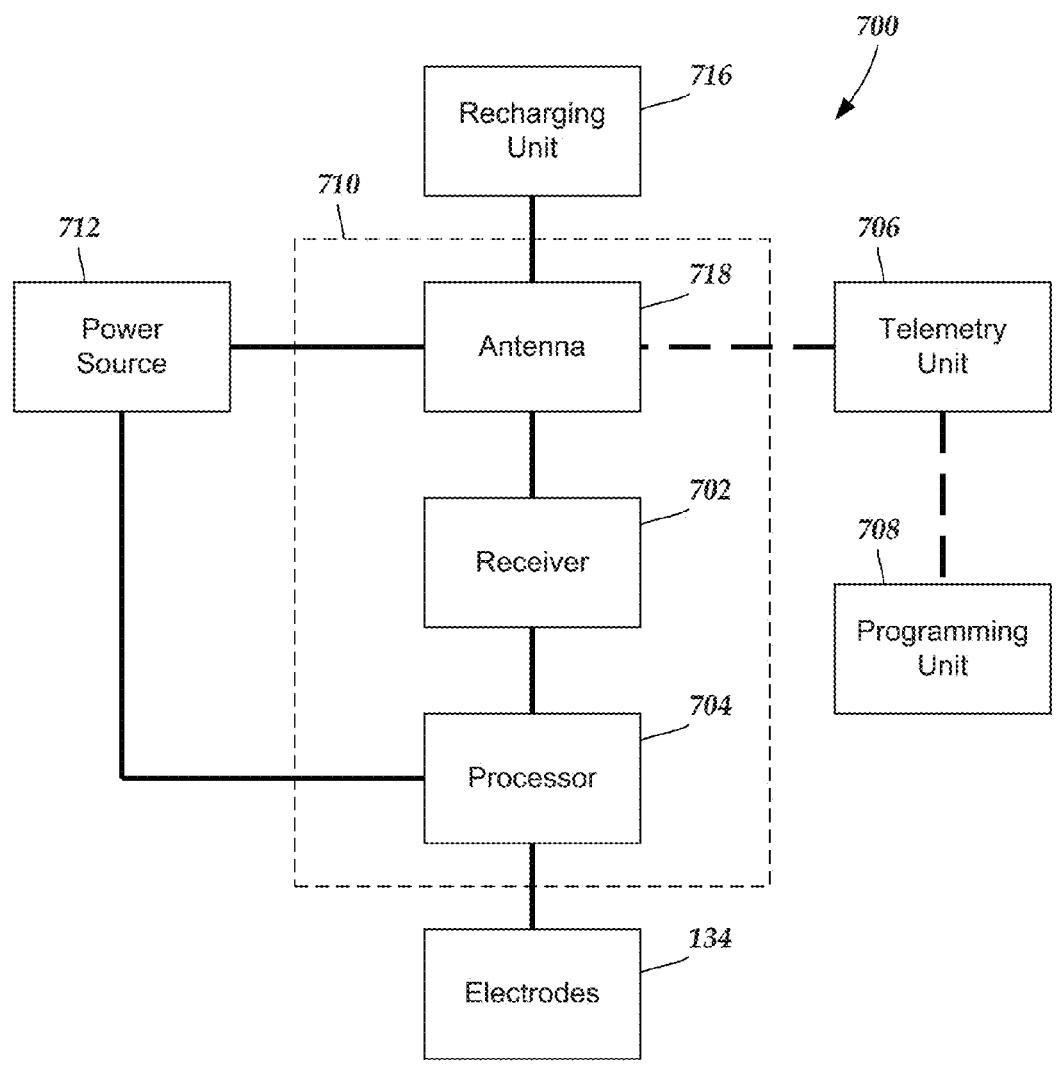
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 selects which electrode(s) are cathodes and which electrode(s) are anodes. In some embodiments, the processor 704 is used to identify which electrodes provide the most useful stimulation of the desired tissue.

Any processor can he used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating Whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable control module for an electrical stimulation system, the control module comprising:
 a connector housing comprising a connector having one or more ports each configured and arranged to receive a proximal end portion of a lead or lead extension and a plurality of connector contacts disposed within the connector and configured and arranged for making contact with terminals disposed on the proximal end portion of the lead or lead extension;
 a metal electronics housing coupled to the connector housing and having a first major surface and a second major surface opposite the first major surface, wherein the metal electronics housing consists of one or two metal sheet, wherein each of one or two metal sheets is bent to form at least a portion of the first major surface and at least a portion of the second major surface, wherein the first major surface has a length and comprises a first sealed seam extending along an entirety of the length of the first major surface;

an electronic subassembly disposed within the metal electronics housing; and a feedthrough assembly disposed between the connector housing and the metal electronics housing and comprising at least one non-conductive block and a plurality of conductive feedthroughs extending through the at least one non-conductive block and electrically coupling the electronic subassembly to the connector contacts.

2. The control module of claim 1, wherein the one or two metal sheets consists of a first metal sheet and a second metal sheet with a second sealed seam extending along an entirety of the length of the second major surface.

3. The control module of claim 2, wherein the first sealed seam and the second sealed seam both join the first metal sheet to the second metal sheet.

4. The control module of claim 1, wherein the feedthrough assembly comprises a metal flange disposed around the at least one non-conductive block and attached to the metal electronics housing.

5. The control module of claim 1, wherein the one or two metal sheets consist of grade 23 titanium alloy.

6. The control module of claim 1, wherein the one or two metal sheets define at least one interlocking feature along the first sealed seam.

7. The control module of claim 6, wherein the at as one interlocking feature is a dovetailed feature.

8. The control module of claim 6, wherein the at least one interlocking feature is a plurality of projections and a plurality of cutouts with the projections interlocking with the cutouts.

9. An electrical stimulation system, comprising:
the control module of claim 1; and
a lead coupleable to the control module comprising a proximal end portion, a distal end portion, a plurality of electrodes disposed along the distal end portion, and a plurality of terminals disposed along the proximal end portion and electrically coupled to the plurality of electrodes.

10. The control module of claim 1, wherein the one or two metal sheets consists of a first metal sheet.

11. The control module of claim 10, wherein the first metal sheet comprises a first edge and a second edge, wherein the first sealed seam joins the first edge to the second edge.

12. An implantable control module for an electrical stimulation system, the control module comprising:
a connector housing comprising a connector having one or more ports each configured and arranged to receive a proximal end portion of a lead or lead extension and a plurality of connector contacts disposed within the connector and configured and arranged for making contact with terminals disposed on the proximal end portion of the lead or lead extension;

a metal electronics housing coupled to the connector housing and consisting of a single metal sheet bent to produce at least a first major surface, wherein the first major surface has a length and comprises a sealed seam extending along an entirety of the length of the first major surface;

an electronic subassembly disposed within the metal electronics housing; and a feedthrough assembly disposed between the connector housing and the metal electronics housing and comprising at least one non-conductive block and a plurality of conductive feedthroughs extending through the at least one non-conductive block and electrically coupling the electronic subassembly to the connector contacts.

13. The control module of claim 12, wherein the single metal sheet defines a first edge and a second edge, wherein the first sealed seam joins the first edge to the second edge.

14. The control module of claim 12, wherein the single metal sheet forms a second major surface opposite the first major surface, at least two side surfaces coupling the first and second major surfaces, and a bottom piece coupling the first major surface to the second major surface and coupling two of the at least two side surfaces.

15. The control module of claim 12, wherein the feedthrough assembly comprises a metal flange disposed around the at least one non-conductive block and attached to the metal electronics housing.

16. The control module of claim 12, wherein the single metal sheet consists of grade 23 titanium alloy.

17. The control module of claim 12, wherein the single metal sheet defines at least one interlocking feature formed along each of at least two edges of the single metal sheet.

18. The control module of claim 12, wherein the at least one interlocking feature is a dovetailed feature.

19. An electrical stimulation system, comprising:
the control module of claim 12; and
a lead coupleable to the control module comprising a proximal end portion, a distal end portion, a plurality of electrodes disposed along the distal end portion, and a plurality of terminals disposed along the proximal end portion and electrically coupled to the plurality of electrodes.

20. The control module of claim 17, wherein the at least one interlocking feature is a plurality of projections and a plurality of cutouts with the projections interlocking with the cutouts.

* * * * *